(12) United States Patent
Suyama (10) Patent No.: US 10,213,096 B2
(45) Date of Patent: Feb. 26, 2019

(54) IMAGE PICKUP APPARATUS AND ENDOSCOPE

(71) Applicant: OLYMPUS CORPORATION, Tokyo (JP)

(72) Inventor: Takuro Suyama, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/650,997

(22) Filed: Jul. 17, 2017

(65) Prior Publication Data

US 2017/0311783 A1 Nov. 2, 2017

Related U.S. Application Data

(63) Continuation of application No. PCT/JP2015/051879, filed on Jan. 23, 2015.

(51) Int. Cl.
*A61B 1/04* (2006.01)
*H01L 27/146* (2006.01)
(Continued)

(52) U.S. Cl.
CPC .............. *A61B 1/042* (2013.01); *A61B 1/005* (2013.01); *A61B 1/0057* (2013.01); *A61B 1/04* (2013.01); *H01L 27/14618* (2013.01); *H01L 27/14636* (2013.01); *A61B 1/0051* (2013.01); *A61B 1/00165* (2013.01); *H04N 2005/2255* (2013.01)

(58) Field of Classification Search
CPC ......... H01L 27/14618; H01L 27/14636; H01L 27/14601; H01L 27/146; G02B 13/001; H04N 5/2253; H04N 5/2257; H04N 5/2254; H04N 2005/2255; A61B 1/042;
(Continued)

(56) References Cited

U.S. PATENT DOCUMENTS

2007/0182843 A1* 8/2007 Shimamura .............. A61B 1/05
348/340
2009/0008732 A1 1/2009 Kojima
(Continued)

FOREIGN PATENT DOCUMENTS

JP 2009-016623 A 1/2009
JP 2009-164481 A 7/2009
(Continued)

OTHER PUBLICATIONS

International Search Report dated Apr. 21, 2015 issued in PCT/JP2015/051879.

*Primary Examiner* — Albert H Cutler
(74) *Attorney, Agent, or Firm* — Scully, Scott, Murphy & Presser, PC (57) ABSTRACT

An image pickup apparatus includes a silicon layer, a rewiring layer including low-permittivity insulating bodies having a permittivity that is lower than a permittivity of silicon oxide, and a cover glass, and a cutout portion is provided in the silicon layer, wirings are provided on the cutout portion, the wirings do not cover at least a part of the low-permittivity insulating bodies in the rewiring layer, the low-permittivity insulating body being exposed at the cutout portion, and the cutout portion is covered by a second protection film including a metal material via a first protection film including an insulating material.

7 Claims, 10 Drawing Sheets

(51) Int. Cl.
  *A61B 1/005* (2006.01)
  *A61B 1/00* (2006.01)
  *H04N 5/225* (2006.01)

(58) Field of Classification Search
  CPC ... A61B 1/005; A61B 1/0057; A61B 1/00165; A61B 1/0051
  See application file for complete search history.

(56) References Cited

U.S. PATENT DOCUMENTS

| | | | |
|---|---|---|---|
| 2009/0200679 A1* | 8/2009 | Harada | H01L 21/76898 257/773 |
| 2011/0127631 A1* | 6/2011 | Kawashima | H01L 27/14603 257/466 |
| 2013/0194464 A1 | 8/2013 | Suzuki et al. | |

FOREIGN PATENT DOCUMENTS

| | | |
|---|---|---|
| JP | 2010-114199 A | 5/2010 |
| JP | 2012-028359 A | 2/2012 |
| JP | 2012-160547 A | 8/2012 |
| JP | 2013-041878 A | 2/2013 |
| JP | 2014-067743 A | 4/2014 |
| WO | WO 2009/004870 A1 | 1/2009 |

\* cited by examiner

IMAGE PICKUP APPARATUS AND ENDOSCOPE

CROSS REFERENCE TO RELATED APPLICATION

This application is a continuation application of PCT/JP2015/051879 filed on Jan. 23, 2015, the entire contents of which are incorporated herein by this reference.

BACKGROUND OF THE INVENTION

1. Field of the Invention

The present invention relates to an image pickup apparatus including a silicon layer in which a light receiving portion is formed, a rewiring layer disposed on the silicon layer, the rewiring layer including a plurality of conductor layers and a plurality of insulating layers each including a low-k material, and a cover glass bonded so as to cover the rewiring layer, and an endoscope including the image pickup apparatus.

2. Description of the Related Art

Chip size package (CSP)-type image pickup apparatuses with a light receiving portion formed on a principal surface, the light receiving portion including, e.g., a CMOS image pickup device, have widely been used in endoscopes because such image pickup apparatuses each have a small diameter. For matching between a light receiving portion including a fine pattern fabricated by a semiconductor technique and large bonding electrodes to which, e.g., a signal cable is connected, a rewiring layer in which a plurality of conductor layers and a plurality of insulating layers are stacked is essential for a CSP-type image pickup apparatus. In the CSP-type image pickup apparatus, a side face of the rewiring layer is exposed at an outer peripheral portion. Also, where, e.g., a through hole is formed in the silicon layer, the rewiring layer is also exposed at a bottom face of the through hole.

In recent years, for enhancement in performance of an image pickup apparatus, use of a material having a relative permittivity k that is lower than a relative permittivity of the silicon oxide, what is called a low-k material, as insulating layers of a rewiring layer has been considered.

Japanese Patent Application Laid-Open Publication No. 2012-28359 discloses a CSP-type semiconductor apparatus in which a through hole is formed in a semiconductor substrate to which a glass substrate is bonded via an adhesive, by etching a back face and a wiring is disposed in the through hole.

SUMMARY OF THE INVENTION

An image pickup apparatus according to an embodiment includes: a silicon layer including a light receiving surface on which light received by a light receiving portion is incident, and an opposed surface on which a plurality of connection terminals are disposed; a rewiring layer disposed on the light receiving surface of the silicon layer, the rewiring layer including a plurality of conductor layers each including conductors electrically connected to the light receiving portion, and a plurality of insulating layers each including a low-permittivity insulating body having a permittivity that is lower than a permittivity of silicon oxide; and a transparent member bonded so as to cover the rewiring layer, and an etched area formed by etching the opposed surface side, the etched area extending to the rewiring layer, is provided in a part of the silicon layer, the image pickup apparatus includes wirings electrically connected to the conductors in the rewiring layer, the conductors being exposed at a bottom face of the etched area, the wirings being provided so as to respectively extend to the connection terminals on the opposed surface via a wall surface of the etched area, and the wirings do not cover at least a part of the insulating layers in the rewiring layer, the insulating layer being exposed at the bottom face of the etched area, and the etched area is covered by a second protection film including a metal material, via a first protection film including an insulating material.

An endoscope according to another embodiment includes an image pickup apparatus in a distal end portion of an insertion portion, the image pickup apparatus including: a silicon layer including a light receiving surface on which light received by a light receiving portion is incident, and an opposed surface on which a plurality of connection terminals are disposed; a rewiring layer disposed on the light receiving surface of the silicon layer, the rewiring layer including a plurality of conductor layers each including conductors electrically connected to the light receiving portion, and a plurality of insulating layers each including a low-permittivity insulating body having a permittivity that is lower than a permittivity of silicon oxide; and a transparent member bonded so as to cover the rewiring layer, an etched area formed by etching the opposed surface side, the etched area extending to the rewiring layer, and being provided in a part of the silicon layer, the image pickup apparatus including wirings electrically connected to the conductors in the rewiring layer, the conductors being exposed at a bottom face of the etched area, the wirings being provided so as to respectively extend to the connection terminals on the opposed surface via a wall surface of the etched area, wherein: the wirings do not cover at least a part of the insulating layers in the rewiring layer, the insulating layer being exposed at the bottom face of the etched area; and the etched area is covered by a second protection film including a metal material, via a first protection film including an insulating material.

DETAILED DESCRIPTION OF THE PREFERRED EMBODIMENT(S)

First Embodiment

As illustrated in FIGS. 1 to 4, an image pickup apparatus 1 according to a first embodiment includes a silicon layer 10, a rewiring layer 20, an adhesive layer 30 and a cover glass 40, which is a transparent member.

It should be noted that the drawings are schematic ones and, e.g., a relationship between a thickness and a width of each part and ratios in thickness and a number of lamination layers among the respective parts are different from actual ones, and parts that are different in dimensional relationship and/or ratio among the drawings may be included in the drawings. Also, illustration and description of some components are omitted. For example, neither illustration nor description of a silicon oxide layer formed on a surface of the silicon layer 10 by oxidative treatment of the silicon layer 10 is provided. Also, the rewiring layer 20 having a multi-layer structure is illustrated in a simplified manner.

Figure 2:
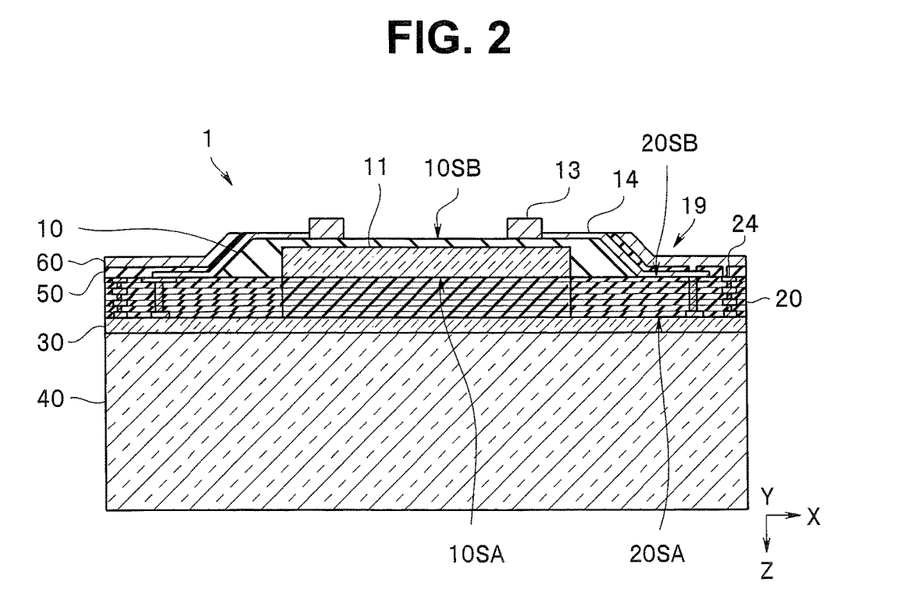
FIG. 2 is a cross-sectional view of the image pickup apparatus according to the first embodiment along line II-II in FIG. 1.

For example, a thickness (Z direction) of the silicon layer 10 is 50 to 100 μm, a thickness of each of the rewiring layer 20 and the adhesive layer 30 is around 5 to 20 μm, and a thickness of the cover glass 40 is 150 μm to 5 mm.

In the silicon layer 10, a light receiving portion 11 including, e.g., a CCD is formed. On an opposed surface 10SB opposed to a light receiving surface 10SA on which light to be received by the light receiving portion 11 is incident, e.g., conductive wires of a signal cable and a plurality of connection terminals 13 are disposed. The cover glass 40 is bonded to the rewiring layer 20 on the light receiving surface 10SA side of the silicon layer 10 via the adhesive layer 30.

Figure 4:
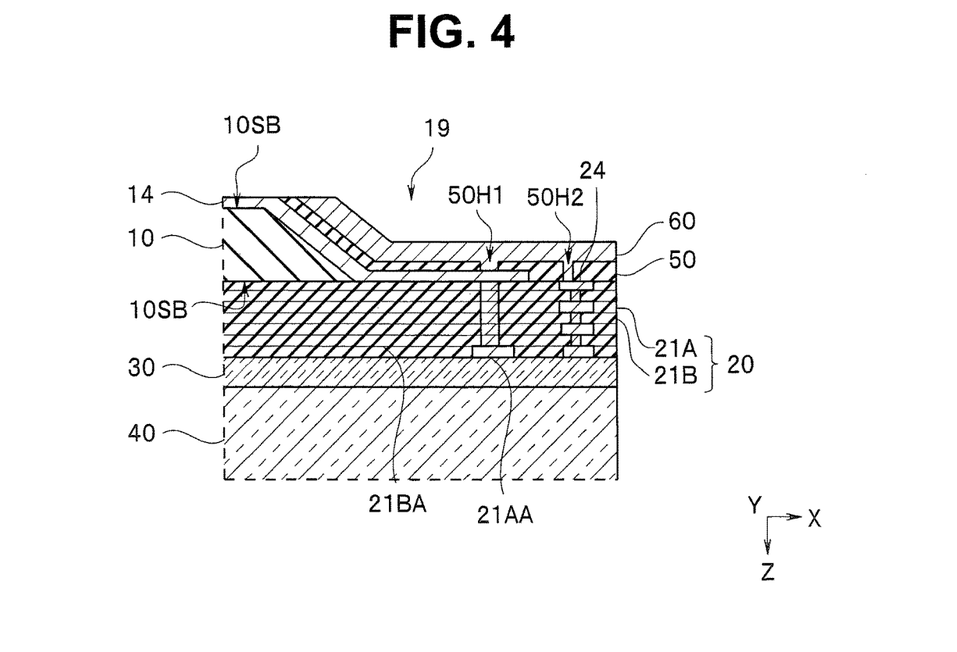
FIG. 4 is a partial cross-sectional view of the image pickup apparatus according to the first embodiment.

The rewiring layer 20 includes a multi-layer wiring in which a plurality of conductor layers 21A and a plurality of insulating layers 21B are stacked. The rewiring layer 20 configures a rewiring circuit for connecting fine wirings in the light receiving portion 11 and the connection terminals 13. Here, as illustrated in FIG. 4, in the rewiring layer 20, each conductor 21AA in each conductor layer 21A is connected to conductors above and below the conductor via a conductor charged in a relevant through hole of the insulating layers 21B. Also, an insulating body 21BA is disposed on a side face of each conductor 21AA in each conductor layer 21A. In other words, each of the conductor layers 21A and the insulating layers 21B is a layer including conductors 21AA and the insulating body 21BA.

In the image pickup apparatus 1, each insulating layer 21B includes a material having a permittivity that is lower than a permittivity of silicon oxide, what is called a low-k material.

A low-k material is inferior in humidity resistance/water resistance, that is, resistance to infiltration of moisture (e.g., water vapor) to conventional insulating layer materials. An image pickup apparatus using a low-k material as insulating layers may have insufficient reliability because of exposure of the low-k material. In other words, infiltration of moisture into the insulating layers including a low-k material causes a rise in relative permittivity and thus an increase in parasitic capacitance, which may result in problems such as an operation failure due to a signal delay and corrosion of conductors in conductor layers.

The low-k material is a material having a relative permittivity k that is lower than a relative permittivity of silicon oxide (k=4.0), and is preferably a material having a relative permittivity k of no more than 3.0. A lower limit value of the relative permittivity k of the low-k material is no less than 1.5, preferably no less than 2.0 according to a technological limit.

In the image pickup apparatus 1, the low-k material of the insulating layers 21B is a porous carbon-doped silicon oxide film (SiOC). Porous SiOC is formed as a porous body including voids because of a structure of porous SiOC and can be made to have a relative permittivity k of 2.7.

For the material of the insulating layers 21B, e.g., a fluorine-doped silicon oxide film (SiOF/FSG), a hydrogen-containing polysiloxane (HSQ)-based material, a methyl-containing polysiloxane (MSQ)-based material or an organic (polyimide-based, parylene-based or fluorine-based) material, other than SiOC, can be used.

Here, it is possible that only a part of the insulating layers, for example, the insulating body in a part that is in contact with the silicon layer 10, includes a low-k material.

The image pickup apparatus 1 is of a chip size package (CSP) type having a small size and high productivity. A CSP-type image pickup apparatus is manufactured by cutting a bonded wafer formed by bonding a semiconductor wafer in which a multitude of light receiving portions 11 are formed and a multitude of rewiring layers 20 are disposed, and a glass substrate to each other. Also, the silicon layer 10 of the image pickup apparatus 1 is fabricated by subjecting a semiconductor wafer to a thinning process in the bonded wafer state.

In the image pickup apparatus 1, which is of the chip size package (CSP) type, the cover glass 40 completely covers a surface 20SA on the light receiving surface side of the rewiring layer 20. Also, as illustrated in, e.g., FIG. 3, a frame-like guard ring 24 extending along outer edges is formed in the rewiring layer 20. The guard ring 24 is formed simultaneously with disposition of the rewiring layer 20, using a conductor 21AA that is the same as the conductors 21AA used in the conductor layers 21A. The guard ring 24 is a moisture-proof wall extending through the rewiring layer 20, and blocks infiltration of moisture into the low-k material inside the guard ring 24.

Then, in the image pickup apparatus 1, a cutout portion 19 is formed at each of end portions of the silicon layer 10, the cutout portion 19 being an etched area reaching the rewiring layer 20, which is formed by etching the opposed surface 10SB side. The removal of the silicon layer 10 is performed to expose the conductors 21AA in the conductor layer 21A of the rewiring layer 20 at a surface 20SB. At a surface of each cutout portion 19, not only the conductors 21AA, but also the insulating layer 21B including the low-k material are exposed.

The conductors 21AA exposed at the cutout portions 19 are connected to wirings 14. The plurality of wirings 14 respectively extend to the connection terminals 13 on the opposed surface 10SB via relevant wall surfaces of the cutout portions 19. In other words, the rewiring layer 20 is connected to the connection terminals 13 via the wirings 14.

In the image pickup apparatus 1, the conductors 21AA are exposed at the surface 20SB by the cutout portions 19, and thus, the image pickup apparatus 1 can easily be manufactured and downsized compared to an image pickup apparatus in which through holes are formed. However, the surfaces of the cutout portions 19 cannot completely covered by metal materials of the wirings 14. This is because the plurality of wirings 14 need to be insulated from one another.

In the image pickup apparatus 1, the surface of each cutout portion 19 is covered by a second protection film 60 including a metal material via a first protection film 50 including an insulating material.

The first protection film 50 includes, for example, silicon oxide or silicon nitride, which have a good humidity resistance compared to the insulating layers 21B. The second protection film 60 includes a conductive material, for example, copper.

The first protection film 50 has a function that, even if the second protection film 60 including a conductor is disposed, ensures insulation of the plurality of wirings 14 below the first protection film 50. Furthermore, a configuration in which two types of protection films having different physical properties are stacked exhibits a good moisture-proof property compared to a protection film including a single type of material. Here, the second protection film 60 may further be covered by a third protection film including an insulating material.

Also, a through hole 50H1 may be formed in the first protection film 50 to electrically connect any of the wirings 14 and the second protection film 60. For example, electrical connection of a wiring 14 connected to a conductor having a ground potential, to the second protection film 60 enhances noise immunity of the image pickup apparatus 1 because of a shielding effect.

Also, a through hole 50H2 may be formed in the first protection film 50 to electrically connect any of the wirings 14 and the guard ring 24. For example, electrical connection of the wiring 14 connected to the conductor having a ground potential, to the guard ring 24 enhances noise immunity of the image pickup apparatus 1 because of a shielding effect.

Here, in the image pickup apparatus 1, the through hole 50H1 and the through hole 50H2 are formed in the first protection film 50, and the second protection film 60 and the guard ring 24 are electrically connected to one wiring 14 having a ground potential.

In the image pickup apparatus 1, the cutout portions 19 are formed on the opposed surface 10SB side for disposition of the plurality of wirings 14. Then, even if the insulating layers 21B of the rewiring layer 20 include a low-k material, infiltration of moisture from the cutout portions 19 is prevented and thus, the image pickup apparatus 1 has high reliability.

Figure 5A:
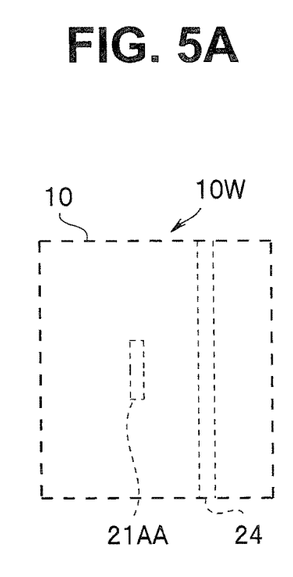
FIG. 5A is a partial top view for describing a method for manufacturing the image pickup apparatus according to the first embodiment.
Figure 5B:
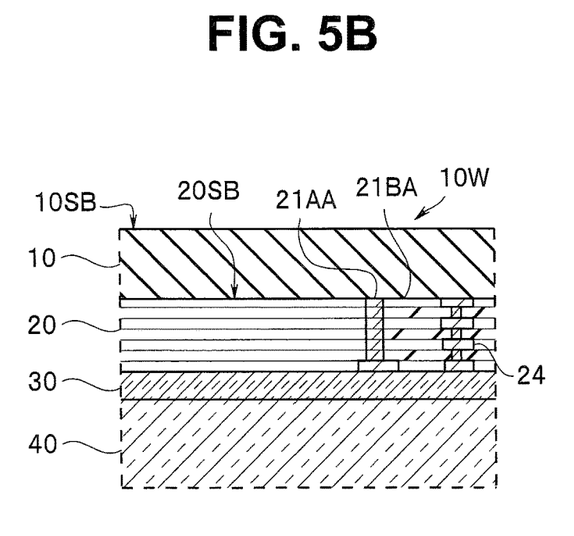
FIG. 5B is a partial cross-sectional view for describing the method for manufacturing the image pickup apparatus according to the first embodiment.
Figure 6A:
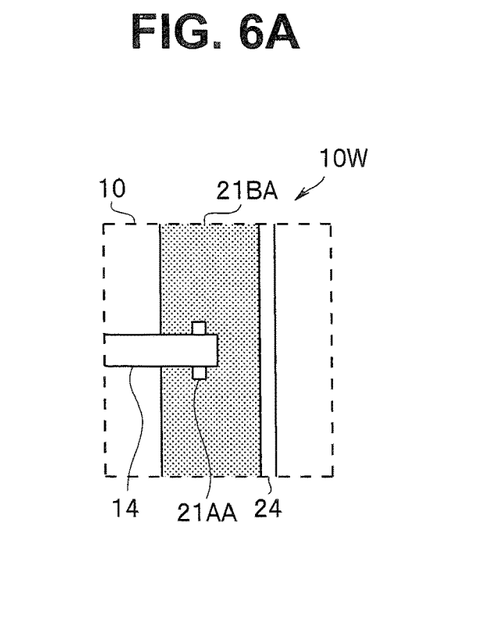
FIG. 6A is a partial top view for describing the method for manufacturing the image pickup apparatus according to the first embodiment.
Figure 6B:
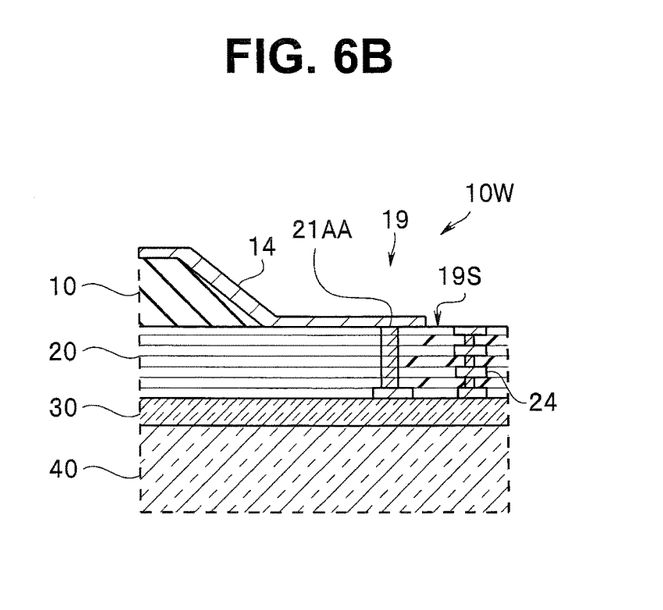
FIG. 6B is a partial cross-sectional view for describing the method for manufacturing the image pickup apparatus according to the first embodiment.
Figure 7A:
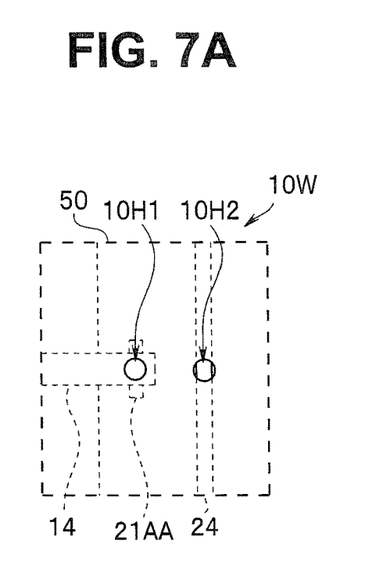
FIG. 7A is a partial top view for describing the method for manufacturing the image pickup apparatus according to the first embodiment.
Figure 7B:
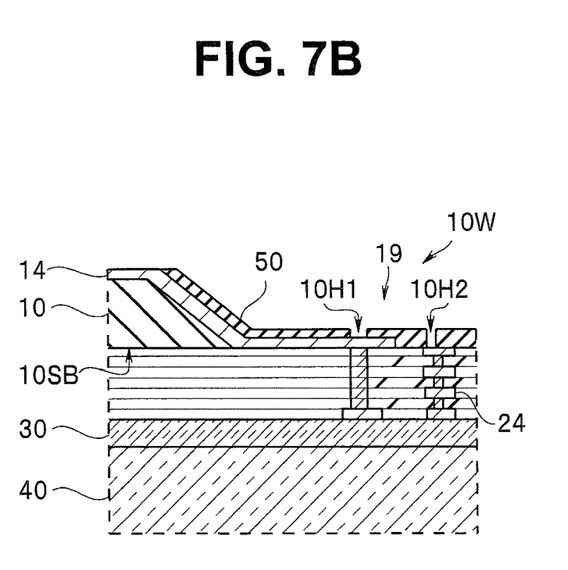
FIG. 7B is a partial cross-sectional view for describing the method for manufacturing the image pickup apparatus according to the first embodiment.

Next, a method for manufacturing the image pickup apparatus 1 will briefly be described. Here, FIGS. 5A, 6A and 7A are top views, FIGS. 5B, 6B and 7B are cross-sectional views of FIGS. 5A, 6A and 7A, respectively. Also, although the steps illustrated in FIGS. 5A to 7B are performed in a bonded wafer state, the description will be provided as individual image pickup apparatuses.

As illustrated in FIGS. 5A and 5B, a bonded wafer 10W including a silicon layer 10, a rewiring layer 20, an adhesive layer 30 and a cover glass 40 is fabricated.

Figure 3:
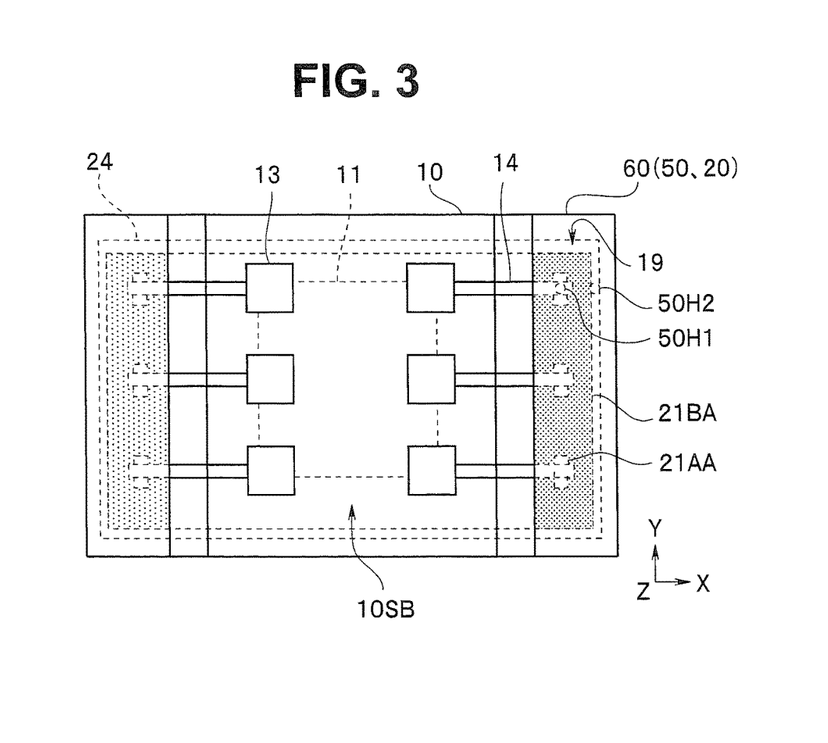
FIG. 3 is a top view of the image pickup apparatus according to the first embodiment.

In fabrication of the bonded wafer 10W, first, semiconductor circuits such as light receiving portions 11 are formed on a silicon wafer. Next, the rewiring layer 20 is disposed on the silicon wafer. Here, as illustrated in FIG. 3, an annular guard ring 24 is formed in the rewiring layer 20 so as to surround each light receiving portion 11.

A material for the guard ring 24 is selected from materials having a good humidity resistance compared to low-k materials, according to a manufacture process and specifications of the image pickup apparatus 1. In the image pickup apparatus 1, the guard ring 24 is a part of the rewiring layer 20, and the guard ring 24 is formed simultaneously with formation of the rewiring layer 20. In other words, the guard ring 24 includes a frame-like layer formed by stacking a plurality of layers according to a process of formation of the rewiring layer 20. Although parts of the insulating layers 21B are present outside the guard ring 24, infiltration of moisture to the inside of the guard ring 24 is prevented.

Then, a bonded wafer is fabricated by bonding a glass wafer to the silicon wafer via an adhesive layer 30. Then, an opposed surface 10SB of the silicon wafer of the bonded wafer is polished to form a silicon layer 10. Here, the adhesive layer 30 includes a transparent resin, such as epoxy resin or silicone resin, having a good humidity resistance compared to a low-k material of the insulating layers 21B. Also, the transparent member may include, e.g., a resin as long as the resin is a material exhibiting a high transmittance for a wavelength range of light to be received by the light receiving portion 11. The transparent member having a sufficiently large thickness blocks infiltration of moisture from the light receiving surface side.

As illustrated in FIG. 5A, each conductor 21AA connected to the light receiving portion 11 is in contact with a face 20SA of the rewiring layer 20, the face 20SA being in contact with the silicon layer 10. A periphery of each conductor 21AA is surrounded by an insulating body 21BA.

Next, end faces of the silicon layer 10 are removed by wet etching using, for example, an alkaline solution such as KOH or TMAH to form cutout portions 19. The etching processing is performed in the wafer state, and thus, more precisely, areas that are to be end faces of the silicon layer 10 in an image pickup apparatus after the wafer being cut into pieces are etched. Since the silicon layer 10 is thinned, etched areas extending to the rewiring layer 20 can easily be formed by etching the opposed surface 10SB side.

Then, as illustrated in FIGS. 6A and 6B, wirings 14 electrically connecting the conductors 21AA exposed at a surface of each cutout portion 19 and relevant connection terminals 13 are disposed. For example, the wirings 14 are in the form of a copper pattern disposed by a sputtering method or a plating method. The wirings 14 extend to the opposed surface 10SB from the relevant etched areas via the side faces of the relevant cutout portions 19. Here, the connection terminals 13 may be disposed simultaneously with the disposition of the wirings 14 or after the disposition of the wirings 14.

Here, as illustrated in FIG. 6A, at a surface 19S, which is an opening portion of each cutout portion 19 on which a plurality of wirings 14 are disposed, not only the wirings 14 but also the insulating body 21BA are exposed.

As illustrated in FIGS. 7A and 7B, the surface 19S of the cutout portion 19 is covered by a first protection film 50 including an insulating material. The first protection film 50 only needs to cover at least the conductor 21AA and the insulating body 21BA at the surface 19S. The first protection film 50 includes, for example, a silicon oxide film formed by a sputtering method, the silicon oxide film having a thickness of no less than 0.5 µm and no more than 10 µm. The first protection film 50 may include an organic substance such as a photoresist.

Then, a second protection film 60 including a metal is further disposed on the first protection film 50. The second protection film 60 includes, for example, a copper film formed by a sputtering method, the copper film having a thickness of no less than 0.5 µm and no more than 10 µm. The second protection film 60 may include a resin containing fine particles of a conductive body such as carbon.

Figure 1:
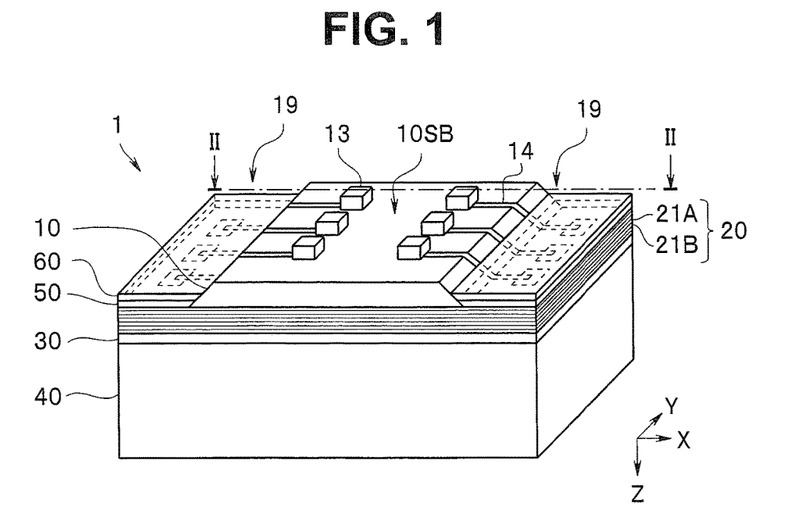
FIG. 1 is a perspective view of an image pickup apparatus according to a first embodiment.

Then, the wafer is diced to cut the wafer into a plurality of image pickup apparatuses 1 such as illustrated in, e.g., FIG. 1.

In the rewiring layer 20 of the image pickup apparatus 1, infiltration of moisture from the side faces is blocked by the guard ring 24, and infiltration of moisture from the light receiving surface 10SA is blocked by the cover glass 40. Then, infiltration of moisture from the cutout portions 19 is blocked by the first protection film and the second protection film.

In other words, the image pickup apparatus 1 prevents infiltration of moisture into the insulating layers and thus have high reliability.

The image pickup apparatus 1 exhibited no property degradation even though the image pickup apparatus 1 was left, for example, in a high-temperature and humidity environment of, for example, 85° C. and a humidity of 85% for 1000 hours.

Modification of First Embodiment

Figure 8:
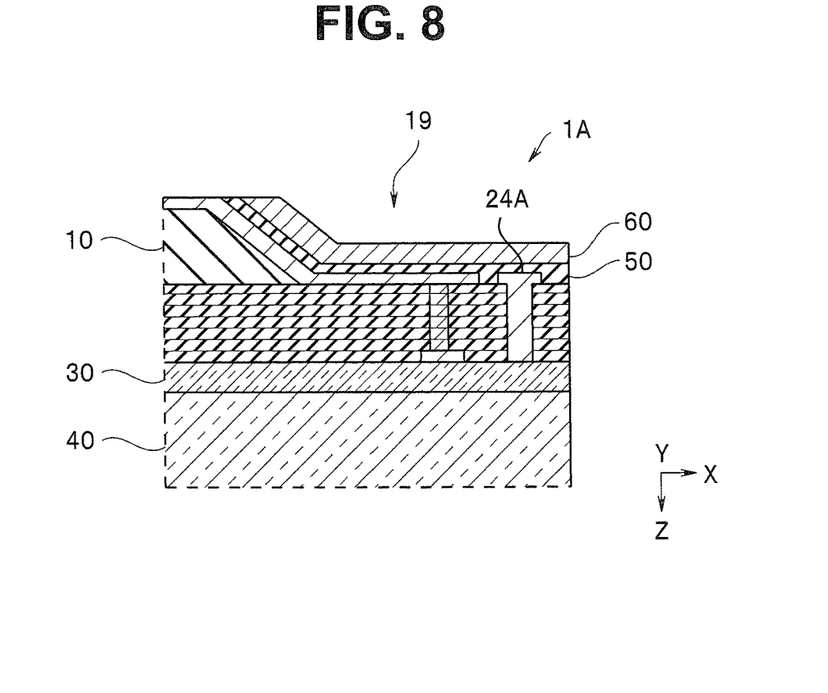
FIG. 8 is a partial cross-sectional view of an image pickup apparatus according to a modification of the first embodiment.

Next, an image pickup apparatus 1A according to a modification of the first embodiment will be described. The image pickup apparatus 1A is similar to the image pickup apparatus 1 according to the first embodiment, and thus, a component having a function that is the same as a function of a component in the first embodiment is provided with a reference numeral that is the same as a reference numeral of the component in the first embodiment, and description of the component will be omitted.

As illustrated in FIG. 8, in the image pickup apparatus 1A, a guard ring 24A is configured by a metal material charged in a trench extending through a rewiring layer 20.

In other words, if no guard ring is formed in the rewiring layer 20, a frame-like trench surrounding a light receiving portion 11 is formed in the rewiring layer 20 after formation of cutout portions 19. The trench extends through the rewiring layer 20 and a bottom face of the trench is an adhesive layer 30.

Then, for example, simultaneously with disposition of wirings 14 including a metal material, for example, copper, copper is charged in the trench. Here, if connection terminals 13 are disposed after disposition of the wirings 14, copper may be charged in the trench simultaneously with the disposition of the connection terminals 13.

Also, in order to block infiltration of moisture from the side faces, the side faces of the image pickup apparatus 1 may be covered by a protection film including at least either an insulating material or a metal material, instead of the guard ring 24. Also, an O-shaped ring may be fitted in the trench.

Each of image pickup apparatuses having a configuration in which infiltration of moisture from cutout portions 19 is blocked by a first protection film and a second protection film and infiltration of moisture from side faces is blocked have the effects of the image pickup apparatus 1.

Second Embodiment

Next, an image pickup apparatus 1B according to a second embodiment will be described. The image pickup apparatus 1B is similar to the image pickup apparatus 1 according to the first embodiment, and thus, a component having a function that is the same as a function of a component in the first embodiment is provided with a reference numeral that is the same as a reference numeral of the component in the first embodiment, and description of the component will be omitted.

Figure 9:
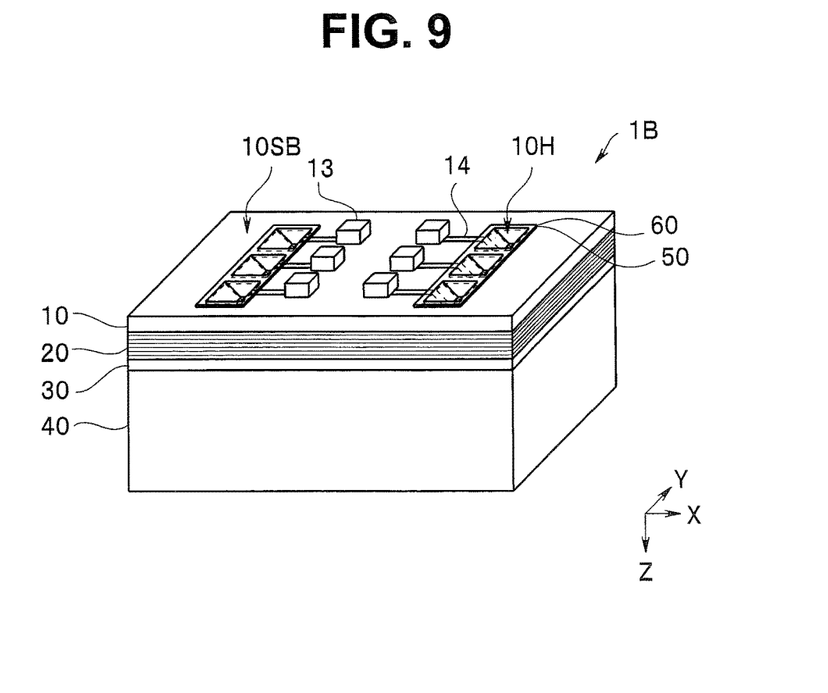
FIG. 9 is a perspective view of an image pickup apparatus according to a second embodiment.
Figure 10:
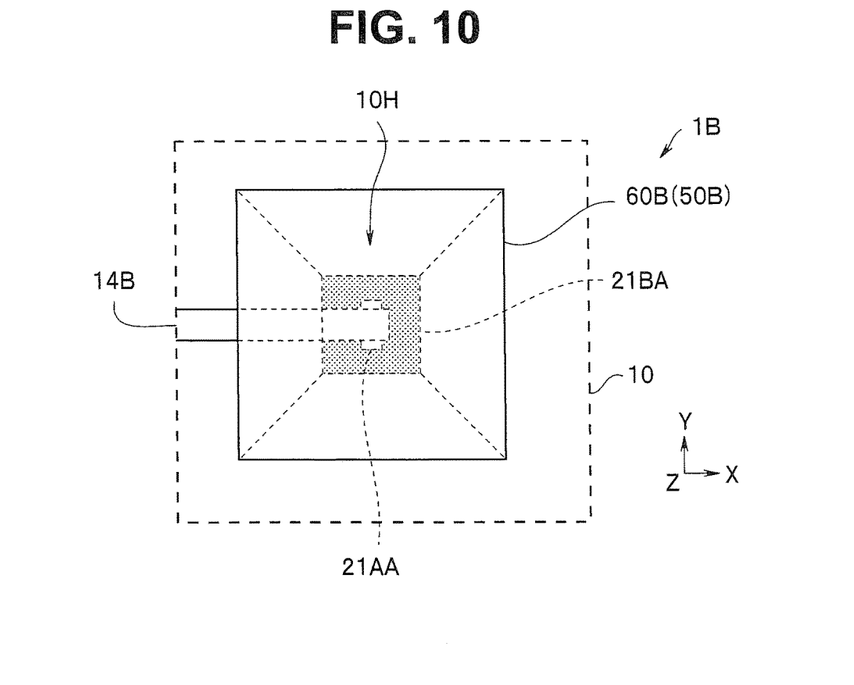
FIG. 10 is a partial top view of the image pickup apparatus according to the second embodiment.
Figure 11:
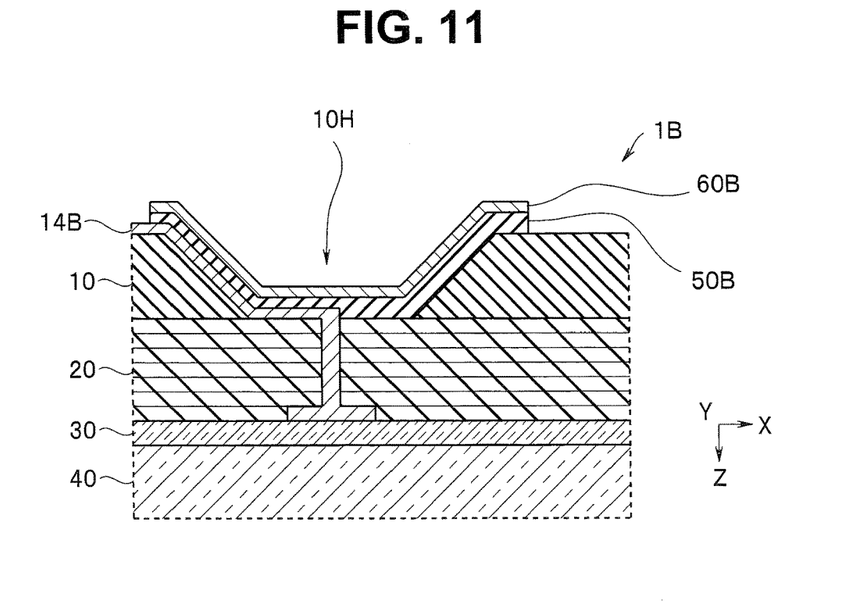
FIG. 11 is a partial cross-sectional view of the image pickup apparatus according to the second embodiment.

As illustrated in FIGS. 9 to 11, in the image pickup apparatus 1B, etched areas are a plurality of through holes 10H extending through a silicon layer 10. Each through hole 10H including wall surfaces that are inclined surfaces are formed by wet etching using an alkaline solution.

As illustrated in FIG. 10, at a bottom face of each through hole 10H, an insulating body 21BA including a low-k material is exposed. However, an opening of each through hole 10H is covered by an insulating layer 50B, which is a first protection film including an insulating material, and a metal layer 60B, which is a second protection, film including a metal material.

Thus, the image pickup apparatus 1B has no possibility of infiltration of moisture into an insulating layer 21B from an opposed surface 10SB side via the through holes 10H and has high reliability as with the image pickup apparatus 1.

Here, the bottom faces of the through holes 10H can be covered by wirings 14B or charged with conductors, which, however, makes the process complicated. On the other hand, the insulating layer 50B and the metal layer 60B can easily be disposed.

Also, the insulating layer 50B and the metal layer 60B only need to cover at least the insulating body 21BA including a low-k material, but may broadly cover not only the openings of the through hole 10H but also the opposed surface 10SB.

Modifications of Second Embodiment

Next, image pickup apparatuses 1C to 1E according to modifications of the second embodiment will be described. The image pickup apparatuses 1C to 1E according to the modifications are similar to the image pickup apparatus 1B according to the second embodiment and have the effects of the image pickup apparatus 1B, and thus, a component having a function that is the same as a function of a component in the second embodiment is provided with a reference numeral that is the same as a reference numeral of the component in the second embodiment, and description of the component will be omitted.

Modification 1 of Second Embodiment

Figure 12A:
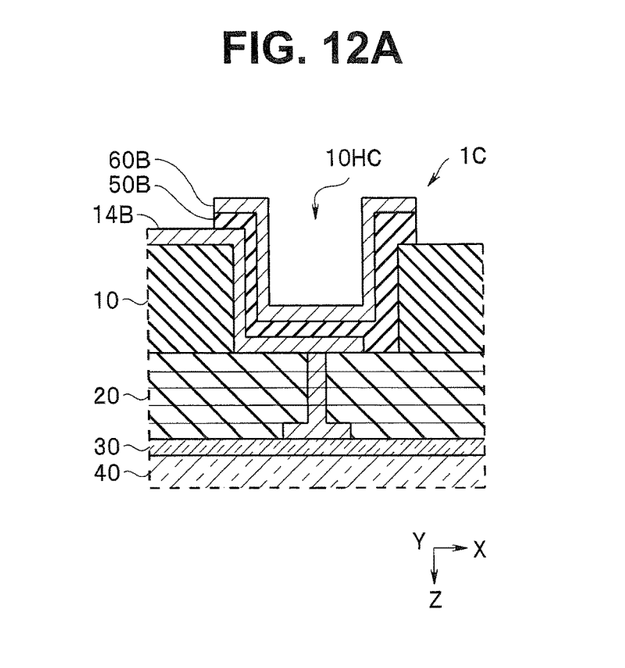
FIG. 12A is a partial cross-sectional view of an image pickup apparatus according to modification 1 of the second embodiment.
Figure 12B:
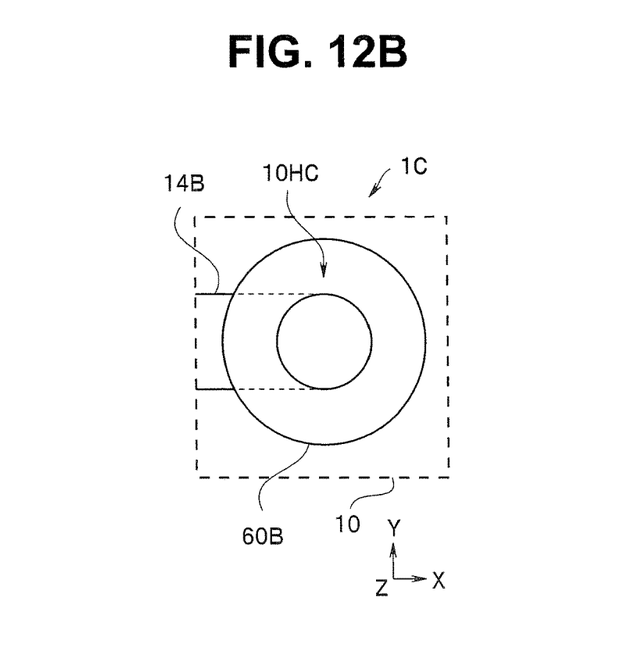
FIG. 12B is a partial top view of the image pickup apparatus according to modification 1 of the second embodiment.

In the image pickup apparatus 1B, the through holes 10H are formed by wet etching, and thus, the wall surfaces form a tapered shape. On the other hand, an image pickup apparatus 1C according to modification 1, which is illustrated in FIGS. 12A and 12B, through holes 10HC are formed by dry etching, and thus, wall surfaces of each through hole 10HC are substantially vertical.

For the dry etching, a fluorine-based gas such as $CF_4$, $CHF_3$ or $C_2F_6$ is used. The through holes 10HC formed by dry etching have a high density compared to the through holes 10H formed by wet etching, and thus, the image pickup apparatus 1C is smaller in size than the image pickup apparatus 1B.

Modifications 2 and 3 of Second Embodiment

A guard ring of an image pickup apparatus may have any shape as long as such shape can prevent infiltration of moisture from side faces. Also, the guard ring may be formed simultaneous with formation of a rewiring layer 20 or may be disposed using a trench extending through the rewiring layer 20.

Figure 13A:
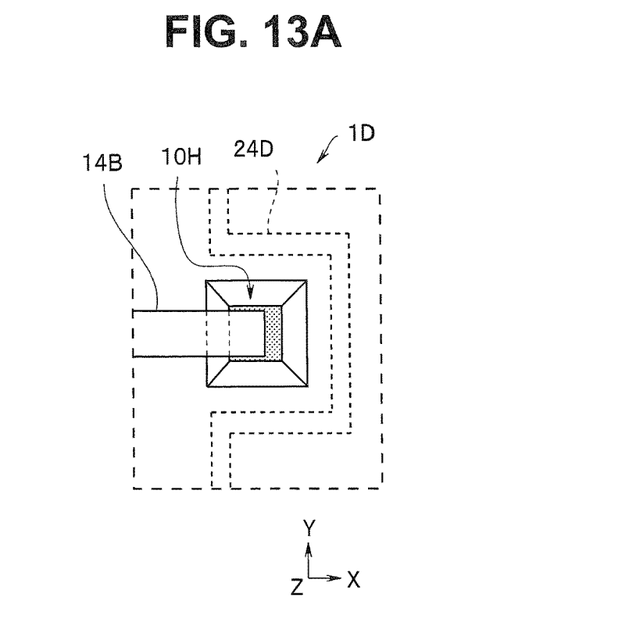
FIG. 13A is a partial top view of an image pickup apparatus according to modification 2 of the second embodiment.

As illustrated in FIG. 13A, a guard ring 24D in an image pickup apparatus 1D according to modification 2 is formed in an annular shape so as to surround each through hole 10H.

Figure 13B:
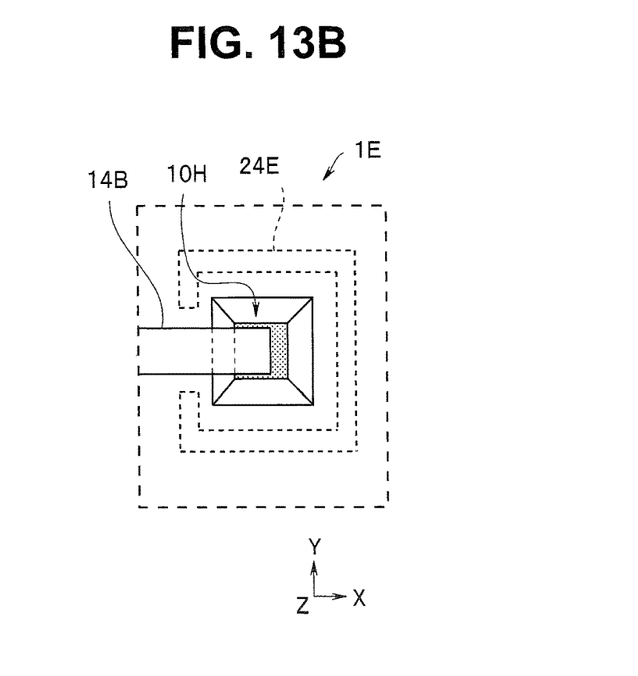
FIG. 13B is a partial top view of an image pickup apparatus according to modification 3 of the second embodiment.

Also, a guard ring 24E in an image pickup apparatus 1E according to modification 3, which is illustrated in FIG. 13B, is formed so as to surround a through hole 10H.

Each of the image pickup apparatuses 1D and 1E each including a first protection film 50 and a second protection film 60 configured to block infiltration of moisture from cutout portions 19 and including respective guard rings 24D and 24E configured to block infiltration of moisture from side faces has the effects of the image pickup apparatus 1.

Third Embodiment

Next, an endoscope system 9 including an endoscope 2 according to a third embodiment will be described.

Figure 14:
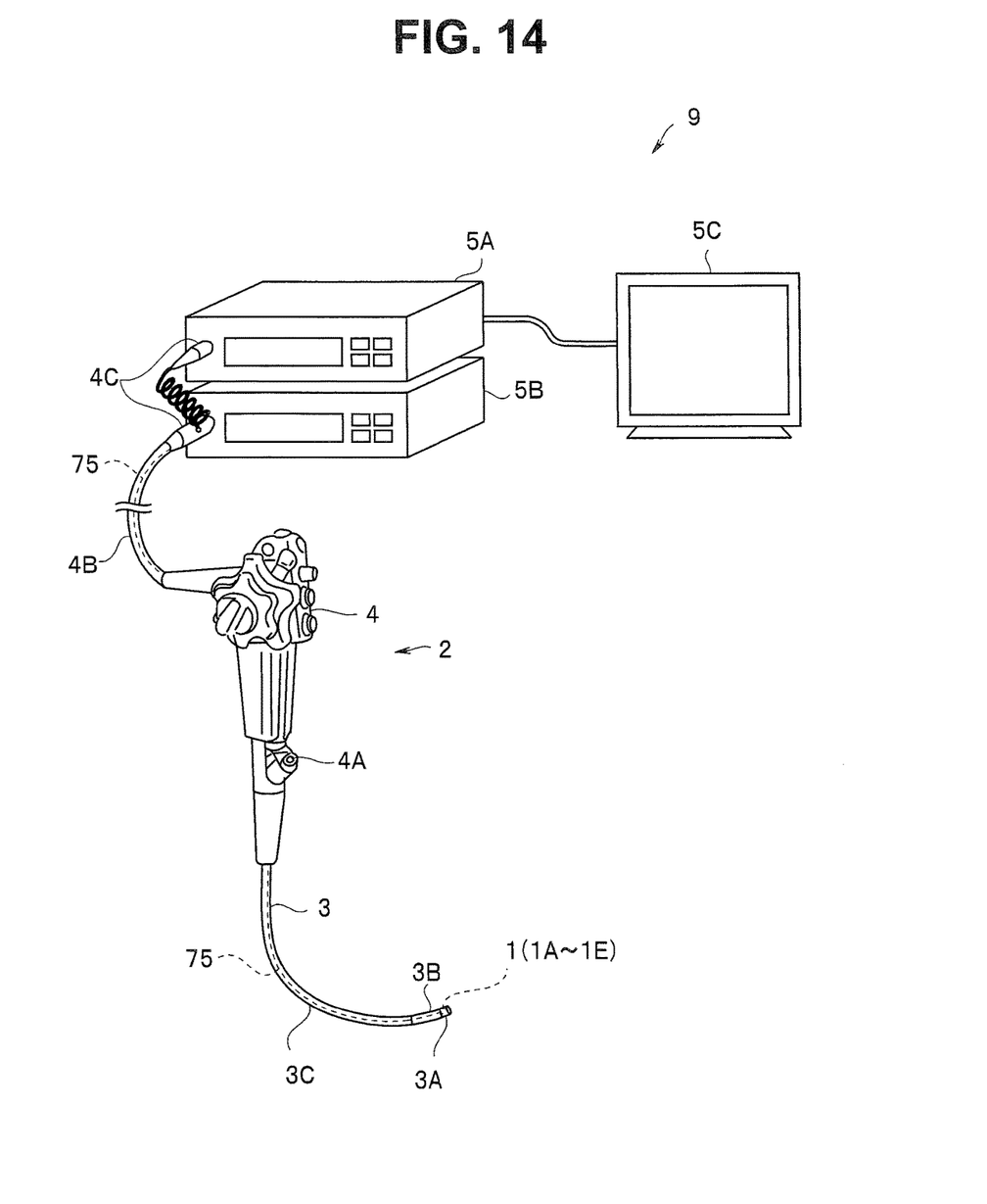
FIG. 14 is a perspective view of an endoscope according to a third embodiment.

As illustrated in FIG. 14, the endoscope system 9 includes the endoscope 2, a processor 5A, a light source apparatus 5B and a monitor 5C. An insertion portion 3 of the endoscope 2 is inserted into a body cavity of a subject to pick up an image of the inside of the body of the subject and output an image pickup signal. In other words, the endoscope 2 includes any of the image pickup apparatuses 1 and 1A to 1E, in a distal end portion of the insertion portion 3.

On a proximal end side of the insertion portion 3 of the endoscope 2, an operation portion 4 provided with various types of buttons for operating the endoscope 2 are disposed. In the operation portion 4, a treatment instrument insertion opening 4A of a channel that allows insertion of a treatment instrument such as a living body forceps, an electric scalpel or an examination probe into a body cavity of a subject.

The insertion portion 3 includes a distal end portion 3A in which the image pickup apparatus 1 is disposed, a bendable bending portion 3B provided so as to be continuous with a proximal end side of the distal end portion 3A, and a flexible tube portion 3C provided so as to be continuous with a proximal end side of the bending portion 3B. The bending portion 3B is bent by operation of the operation portion 4.

A universal cord 4B provided on a proximal end portion side of the operation portion 4 allows insertion of a signal cable 75 connected to the image pickup apparatus 1 of the distal end portion 3A.

The universal cord 4B is connected to the processor 5A and the light source apparatus 5B via a connector 4C. The processor 5A controls the entire endoscope system 9, and performs signal processing of an image pickup signal outputted by the image pickup apparatus 1 and outputs the resulting signal as an image signal. The monitor 5C displays the image signal outputted by the processor 5A.

The light source apparatus 5B includes, for example, a white LED. White light emitted by the light source apparatus 5B is guided to an illumination optical system 3D of the distal end portion 3A via a light guide (not illustrated) inserted through the universal cord 4B and illuminate an object.

The endoscope 2 includes any of the image pickup apparatuses 1 and 1A to 1E having high reliability, in the distal end portion of the insertion portion and thus has high reliability.

The present invention is not limited the above-described embodiments, modifications, etc., and various changes, alterations, etc., are possible without departing from the spirit of the present invention.

What is claimed is:

1. An image pickup apparatus comprising:
a silicon layer including a light receiving surface on which light received by a light receiving portion is incident, and an opposed surface on which a plurality of connection terminals are disposed;
a rewiring layer disposed on the light receiving surface of the silicon layer, the rewiring layer including a plurality of conductor layers each including conductors electrically connected to the light receiving portion, and a plurality of insulating layers each including a low-permittivity insulating body having a permittivity that is lower than a permittivity of silicon oxide; and
a transparent member bonded so as to cover the rewiring layer,
an etched area formed by etching the opposed surface side, the etched area extending to the rewiring layer, and being provided in a part of the silicon layer,
the image pickup apparatus including wirings electrically connected to the conductors in the rewiring layer, the conductors being exposed at a bottom face of the etched area, the bottom face being an insulating layer of the plurality of insulating layers in the rewiring layer, the wirings being provided so as to respectively extend to the connection terminals on the opposed surface via a wall surface of the etched area, wherein:
the wirings do not cover at least a part of the insulating layer of the plurality of insulating layers at the bottom face of the etched area, the at least part of the insulating layer being exposed at the bottom face of the etched area;
the etched area is covered by a second protection film including a metal material, via a first protection film including an insulating material; and
the etched area is one of a cutout portion at an end portion of the silicon layer or a through hole extending through the silicon layer.

2. The image pickup apparatus according to claim 1, wherein any of the plurality of conductors in the rewiring layer and the second protection film is electrically connected via a through hole in the first protection film.

3. The image pickup apparatus according to claim 1, wherein the wirings and the second protection film include a same material.

4. The image pickup apparatus according to claim 1, wherein a guard ring extending along an outer edge is formed in the rewiring layer.

5. The image pickup apparatus according to claim 4, wherein the second protection film and the guard ring are electrically connected via a through hole in the first protection film.

6. The image pickup apparatus according to claim 4, wherein the guard ring includes a metal material charged in a trench extending through the rewiring layer.

7. An endoscope comprising an image pickup apparatus in a distal end portion of an insertion portion, the image pickup apparatus including:
 a silicon layer including a light receiving surface on which light received by a light receiving portion is incident, and an opposed surface on which a plurality of connection terminals are disposed;
 a rewiring layer disposed on the light receiving surface of the silicon layer, the rewiring layer including a plurality of conductor layers each including conductors electrically connected to the light receiving portion, and a plurality of insulating layers each including a low-permittivity insulating body having a permittivity that is lower than a permittivity of silicon oxide; and
 a transparent member bonded so as to cover the rewiring layer,
 an etched area formed by etching the opposed surface side, the etched area extending to the rewiring layer, and being provided in a part of the silicon layer,
 the image pickup apparatus including wirings electrically connected to the conductors in the rewiring layer, the conductors being exposed at a bottom face of the etched area, the bottom face being an insulating layer of the plurality of insulating layers in the rewiring layer, the wirings being provided so as to respectively extend to the connection terminals on the opposed surface via a wall surface of the etched area, wherein:
the wirings do not cover at least a part of the insulating layer of the plurality of insulating layers at the bottom face of the etched area, the at least part of the insulating layer being exposed at the bottom face of the etched area; and the etched area is covered by a second protection film including a metal material, via a first protection film including an insulating material; and
the etched area is one of a cutout portion at an end portion of the silicon layer or a through hole extending through the silicon layer.

* * * * *